(12) United States Patent
Sommerich et al.

(10) Patent No.: US 8,795,710 B2
(45) Date of Patent: Aug. 5, 2014

(54) COLLAGEN DEVICE AND METHOD OF PREPARING THE SAME

(75) Inventors: Robert E. Sommerich, Norton, MA (US); Laurel R. Macomber, North Attleboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 991 days.

(21) Appl. No.: 12/196,621

(22) Filed: Aug. 22, 2008

(65) Prior Publication Data
US 2009/0030526 A1  Jan. 29, 2009

Related U.S. Application Data

(63) Continuation of application No. 11/171,638, filed on Jun. 30, 2005, now abandoned, which is a continuation-in-part of application No. 10/955,835, filed on Sep. 30, 2004, now abandoned.

(60) Provisional application No. 60/542,968, filed on Feb. 9, 2004, provisional application No. 60/565,747, filed on Apr. 27, 2004.

(51) Int. Cl.
*A61F 2/02* (2006.01)

(52) U.S. Cl.
USPC ........ 424/426; 602/50; 623/23.75; 623/23.76

(58) Field of Classification Search
None
See application file for complete search history.

(56) References Cited

U.S. PATENT DOCUMENTS

| | | | |
|---|---|---|---|
| 2,465,357 A | 3/1949 | Correll | |
| 2,492,458 A | 12/1949 | Bering | |
| 3,157,524 A | 11/1964 | Artandi | |
| 3,364,200 A | 1/1968 | Aston et al. | |
| 3,366,440 A | 1/1968 | Nuwayser | |
| 3,520,402 A | 7/1970 | Nichols | |
| 3,526,228 A | 9/1970 | Lyng | |
| 3,632,361 A | 1/1972 | Battista | |
| 3,742,955 A | 7/1973 | Battista et al. | |
| 3,800,792 A | 4/1974 | McKnight et al. | |
| 3,939,831 A | 2/1976 | Cioca et al. | |
| 4,006,220 A | 2/1977 | Gottlieb | |
| 4,016,877 A | 4/1977 | Cruz, Jr. et al. | |
| 4,016,887 A | 4/1977 | Uroshevich | |
| 4,066,083 A | 1/1978 | Ries et al. | |
| 4,089,333 A | 5/1978 | Utsuo et al. | |
| 4,140,537 A | 2/1979 | Luck et al. | |
| 4,148,664 A | 4/1979 | Cruz, Jr. | |
| 4,185,011 A | 1/1980 | Eckmayer et al. | |
| 4,215,200 A | 7/1980 | Miyata et al. | |
| 4,233,360 A | 11/1980 | Luck et al. | |
| 4,238,480 A | 12/1980 | Sawyer | |
| 4,271,070 A | 6/1981 | Miyata et al. | |
| 4,280,954 A | 7/1981 | Yannas et al. | |
| 4,294,241 A | 10/1981 | Miyata et al. | |
| 4,376,071 A | 3/1983 | Jennings et al. | |
| 4,404,033 A | 9/1983 | Steffan | |
| 4,404,970 A | 9/1983 | Sawyer | |
| 4,407,787 A | 10/1983 | Stemberger | |
| 4,412,947 A | 11/1983 | Cioca | |
| 4,522,753 A | 6/1985 | Yannas et al. | |
| 4,578,067 A | 3/1986 | Cruz, Jr. | |
| 4,597,762 A | 7/1986 | Walter et al. | |
| 4,600,533 A | 7/1986 | Chu | |
| 4,606,910 A | 8/1986 | Sawyer | |
| 4,655,980 A | 4/1987 | Chu | |
| 4,689,399 A | 8/1987 | Chu | |
| 4,725,671 A | 2/1988 | Chu et al. | |
| 4,738,849 A | 4/1988 | Sawyer | |
| 4,787,900 A | 11/1988 | Yannas | |
| 4,798,800 A | 1/1989 | Timpl et al. | |
| 4,837,285 A | 6/1989 | Berg et al. | |
| 4,931,546 A | 6/1990 | Tardy et al. | |
| 4,947,840 A | 8/1990 | Yannas et al. | |
| 4,948,540 A | 8/1990 | Nigam | |
| 4,950,483 A | 8/1990 | Ksander et al. | |
| 4,963,146 A | 10/1990 | Li | |
| 4,970,298 A | 11/1990 | Silver et al. | |
| 5,019,087 A | 5/1991 | Nichols | |

(Continued)

FOREIGN PATENT DOCUMENTS

| | | |
|---|---|---|
| CA | 2140834 A1 | 7/1995 |
| EP | 0428541 A1 | 5/1991 |

(Continued)

OTHER PUBLICATIONS

Laquerriere, A., et al., "Experimental Evaluation of Bilayered Human Collagen as a Dural Substitute" Journal of Neurosurgery, vol. 78, No. 3, (Jan. 1, 1993), pp. 487-491, XP009035175.
D. Thompson et al., Haemorrhage Associated with Silastic Dural Substitute, J. of Neurology, Neurosurgery & Psychiatry; 1994; 57:646-648.
Taylor & McConnell; Unconventional Transmissible Agents in Dura Matter; Significance for Lastrogenic Creulzfeldt-Jakob Disease; Neuropathology & Applied Neurobioology, 1996, 22. 259-260.
D.G. Kline, Dural Replacement with Resorbable Collagen: Arch Surg-vol. 91. Dec. 1965, pp. 924-929.
Transmission of Creutzfeldt—Jakob disease by handling of dura matter; The Lancet, vol. 34; Jam 9, 1993, pp. 123-124.
Janetta & Whayne; Formaldehyde-Treated Regenerated Collagen Film and Film-Laminate as a Substitute for Dura Mater/Neurologic Surgery, Vo. XVI, pp. 435-437.

(Continued)

*Primary Examiner* — Marsha Tsay
(74) *Attorney, Agent, or Firm* — Mintz Levin Cohn Ferris Glovsky and Popeo, P.C.

(57) ABSTRACT

A laminated, bioimplantable dural graft product is configured for use as both an onlay graft and a suturable graft. The dural graft product is sufficiently pliable so as to sufficiently conform to a curvature of a tissue surface to which it is applied, such as the curved surface of a meningeal membrane. The use of the graft product can have improved properties, including suture retention strength and fluid impermeability. To use the dural graft product as an implant to replace, reinforce or strengthen bodily tissue, or to act as an adhesion barrier, the dural graft is placed in contact with bodily tissue and conforms to the curvature of the bodily tissue. Sutures can be used to maintain the contact between the dural graft and the bodily tissue.

18 Claims, 6 Drawing Sheets

(56) References Cited

U.S. PATENT DOCUMENTS

| | | |
|---|---|---|
| 5,028,695 A | 7/1991 | Eckmayer et al. |
| 5,071,878 A | 12/1991 | Herschler |
| 5,110,604 A | 5/1992 | Chu et al. |
| 5,171,574 A | 12/1992 | Kuberasampath et al. |
| 5,201,745 A | 4/1993 | Tayot et al. |
| 5,206,028 A | 4/1993 | Li |
| 5,209,776 A | 5/1993 | Bass et al. |
| 5,215,904 A | 6/1993 | Gould et al. |
| 5,227,301 A | 7/1993 | Turner et al. |
| 5,318,779 A | 6/1994 | Hakamatsuka et al. |
| 5,412,076 A | 5/1995 | Gagnieu et al. |
| 5,418,222 A | 5/1995 | Song et al. |
| 5,512,301 A | 4/1996 | Song et al. |
| 5,531,791 A | 7/1996 | Wolfinbarger, Jr. |
| 5,567,806 A | 10/1996 | Abdul-Malak et al. |
| 5,571,216 A | 11/1996 | Anderson |
| 5,580,923 A | 12/1996 | Yeung et al. |
| 5,667,839 A | 9/1997 | Berg |
| 5,677,839 A | 10/1997 | Kondo et al. |
| 5,756,678 A | 5/1998 | Shenoy et al. |
| 5,895,412 A | 4/1999 | Tucker |
| 5,931,800 A | 8/1999 | Rasmussen et al. |
| 5,997,895 A | 12/1999 | Narotam et al. |
| 6,149,609 A | 11/2000 | Lieberman et al. |
| 6,270,793 B1 | 8/2001 | Van Dyke et al. |
| 6,274,155 B1 | 8/2001 | Van Dyke et al. |
| 6,361,551 B1 | 3/2002 | Torgerson et al. |
| 6,375,672 B1 | 4/2002 | Aksan et al. |
| 6,454,787 B1 | 9/2002 | Maddalo et al. |
| 6,461,628 B1 | 10/2002 | Blanchard et al. |
| 6,500,464 B2 | 12/2002 | Ceres et al. |
| 6,706,684 B1 | 3/2004 | Bayon et al. |
| 6,939,562 B2 | 9/2005 | Spiro et al. |
| 7,121,999 B2 | 10/2006 | Abraham et al. |
| 7,429,241 B2 | 9/2008 | Sommerich |
| 8,039,591 B2 | 10/2011 | Sommerich |
| 2002/0103542 A1 | 8/2002 | Bilbo |
| 2003/0014126 A1 | 1/2003 | Patel et al. |
| 2003/0130747 A1 | 7/2003 | Abraham et al. |
| 2003/0220334 A1 | 11/2003 | Wender et al. |
| 2004/0028738 A1 | 2/2004 | Huang et al. |
| 2005/0008660 A1 | 1/2005 | Kipke et al. |
| 2005/0175659 A1 | 8/2005 | Macomber et al. |
| 2005/0226856 A1 | 10/2005 | Ahlfors |
| 2005/0283256 A1 | 12/2005 | Sommerich et al. |
| 2006/0029633 A1 | 2/2006 | Kaiser et al. |
| 2007/0073415 A1 | 3/2007 | Sommerich |
| 2008/0208359 A1 | 8/2008 | Sommerich |
| 2009/0269413 A1 | 10/2009 | Sommerich |

FOREIGN PATENT DOCUMENTS

| | | |
|---|---|---|
| EP | 0667352 | 8/1995 |
| EP | 0440198 | 11/1995 |
| EP | 0681431 A1 | 11/1995 |
| EP | 0742018 | 11/1996 |
| EP | 0877761 | 8/1997 |
| EP | 0 943 346 A1 | 9/1999 |
| EP | 1 084 720 A1 | 3/2001 |
| EP | 1 364 627 A1 | 11/2003 |
| EP | 1 484 070 A1 | 12/2004 |
| EP | 1561480 A2 | 8/2005 |
| EP | 1738780 A2 | 1/2007 |
| JP | 08041425 | 2/1996 |
| JP | 2000-093497 A | 4/2000 |
| JP | 2000-210376 A | 8/2000 |
| JP | 2001-112799 A | 4/2001 |
| JP | 2004148014 A | 5/2004 |
| WO | WO9913902 | 3/1993 |
| WO | 9416570 A1 | 8/1994 |
| WO | WO9420133 | 9/1994 |
| WO | WO9617633 | 6/1996 |
| WO | WO9625961 | 8/1996 |
| WO | 9638541 A1 | 12/1996 |
| WO | 9640174 | 12/1996 |
| WO | WO9649174 | 12/1996 |
| WO | WO9728192 | 8/1997 |
| WO | WO9728193 | 8/1997 |
| WO | WO9737694 | 10/1997 |
| WO | 98/22157 A1 | 5/1998 |
| WO | 9961518 A1 | 12/1999 |
| WO | 01/66162 A1 | 9/2001 |
| WO | 2004/078120 A2 | 9/2004 |
| WO | 2006/066327 A1 | 6/2006 |

OTHER PUBLICATIONS

Collins et al.; Use of Collagen Film as Dural Substitute; Preliminary Animal Studies; J. of Biomedical Material Research, vol. 25, 267-276 (1991).
Doillon et al.; Chemical Inactivators as Sterilization Agents for Bovine Collagen Materials (abstract) in National Library of Medicine Medline Database; TBIA Jan. 15, 2003 (abstract).
Dormont, D.; How to Limit the Spread of Creutzfeldt-Jakob Disease; (abstract) in National Library of Medicine Medline Database; TBIA Jan. 15, 2003 (abstract).
Rohwer, R.G. Analysis of Risk to Biomedical Products Developed from Animal Sources (with Special Emphases on the Spongiform Encephalopathy Agents, Scrapie and BSE); National Library of Medicine Medline Database, TBIS Jan. 15, 2003 (abstract).
Safar, J. et al.; Thermal Stability and Conformational Transitions of Scrapie Amyloid (Prion) Protein Correlatged with Infectivity; National Library of Medicine Medline Databse, TBIS Jan. 15, 2003 (abstract).
Taylor, D.M.; Inactiviation of SE Agents; National Library of Medicine Medline Database TBIS Jan. 15, 2003 (abstract).
Ernst & Race; Comparative Analysis of Scrapie Agent Inactivation Methods; National Library of Medicine MEDLINE Database, TBIS Jan. 15, 2003 (abstract).
DiMartino et al.; Inactivation of the Scrapie Agent in a Scaled-down Procedure for the Purification of *Gangliosidesa* from Brain Tissue; National Library of Medicine MEDLINE Database, TBIS Jan. 15, 2003 (abstract).
Tateishi et al.; Practical Methods for chemical Inactivation of Creutzfeldt—Jakob Disease Parhogen; National Library of Medicine MEDLINE Database, TBIS Jan. 15, 2003 (abstract).
Taylor, D. M.; Inactivation of BSE Agent; National Library of Medicine MEDLINE Database, TBIS Jan. 15, 2003 (abstract).
Brown et al.; A Simple and Effective Method for Inactivating Virus Infectivity in Formalin-fixed Tissue Samples from Patients with Creutzfildt—Jakob Disease' National Library of Medicine MEDLINE Database, TBIS Jan. 15, 2003 (abstract).
Dees et al.; Inactivation of the Scrapie Agent by Ultraviolet Irradiation in the Presence of Chlorpromazine; National Library of Medicine MEDLINE Database, TBIS Jan. 15, 2003 (abstract).
Cho, H. J.; Inactivation of the Scrapie Agent by Pronase; National Library of Medicine MEDLINE Database, TBIS Jan. 15, 2003 (abstract).
Brown et al.; Effect of Chemicals, Heat and Histgopathologic Processing on High-Infectivity Hamster-Adapted Scrapie Viirus; National Library of Medicine MEDLINE Database, TBIS Jan. 15, 2003 (abstract).
Li, Shu-Tung; Peripheral Nerve Repair with Collagen Conduits; Clin. Materials 9 (1992) 195-200.
Madison et al.; Factors Contributing to Preferential Motor Reinnervation in the Primate Peripheral Nervous System; J. of Neuroscioence, Dec. 15, 1999, vol. 19 (24); 11007-11016.
Archibald et al., A Collagen Based Nerve Guide Conduit for Peripheral Nerve Repair; An Electrophgysiological Study of Nerve Regeration in Rodents and Nonhuman Primates; J. of Comparative Neuroology 306; 685-696 (1991).
Archibald et al.; Monkey Median Nerve Repaired by Nerve Graft or Collagen Nerve Guide Tube; J. of Neuroscience, May 1995, 15(5) 4109-4123.
Narotam et al., J. Neurosurgery (1995), 92, p. 406-412.
Narotam et al., British J. of Neurosurgery (1993), 7, p. 635-641.
Ishkawa, H. et al, Rinsho to Kenkyu, Clinical Study and Investigation, vol. 61, No. 4, pp. 1315-1321 (1984).

(56) References Cited

OTHER PUBLICATIONS

Notification of the Safety Requirements for Drugs Produced of Body Components of Cattle, Sheep or Goats to Avoid the Risk of Transmission of BSE or Scrapie (Fed. Reg. No. 40, Feb. 26, 1994).

Notification on the Marketing Authorisation and registration of drugs, Measures to avert risks associated with drugs, stage II (German Federal Institute for Drugs and medical Products, Mar. 28, 1996).

Stein, M. et al., Collagen Sponge as a Topical Hemostatic Agent in Mucogingival Surgery, J. Periodontol, pp. 35-38 (Jan. 1985).

Abbott, W., and Dupree Jr., E., Clinical results of lyophilized human cadaver dura transplantation, J. Neurosurg., vol. 34, pp. 770-773 (Jun. 1971).

Adegbite et al., The role of neomembranes in formation of hematoma around Silastic dura substitute, J. Neurosurg., vol. 58, pp. 295-297 (Feb. 1983).

Amundson, G., Minimizing Blood Loss During Thoracolumbar Spine Surgery, Surgery for Spinal Cord Injuries 45-69 (S. Garfin & B. Northrup eds., 1993).

Anson et al, Bovine pericardium for dural grafts: clinical results in 35 patients, Neurosurgery, vol. 39, No. 4, pp. 764-768 (Oct. 1996).

Archibald et al, Semi-Permeable Collagen Based Nerve Guide Tubes are as Effective as Standard Nerve Grafts to Repair Transected Peripheral Nerves: An Electrophysiological Study in the Non-Human Primate, Soc. Neuro. Abs., vol. 15, p. 318 (1989).

Avery, N. and Bailey, A, An Efficient Method for the Isolation of Intramuscular Collagen, Meat Science, vol. 41, No. 1, pp. 97-100 (1995).

Brown et al.,"Newer Data on the Inactivation of Scrapie Virus or Creutzfeldt-Jakob Disease Virus in Brain Tissue", J. Infectious Dis., vol. 153, No. 6, pp. 1145-48 (Jun. 1986).

BSE Transmission and Medicines, Reg. Affairs J., pp. 207-209 (Mar. 1992).

Campbell et al., Clinical use of freeze-dried human dura matter. J. Neurosurg., vol. 15, No. 2, pp. 208-214 (1958).

Cantore et al., Neurosurgical use of human dura matter sterilized by gamma rays and stored in alcohol: long-term results, J. Neurosurg. vol. 66, pp. 93-95 (Jan. 1987).

Chvapil, M., Collagen sponge: Theory and practice of medical applications, J. Biomed. Mater. Res., vol. 11, pp. 721-741 (1977).

Commission of the European Communities, Ad Hoc Working Party on Biotechnology/Pharmacy, Note for Guidance: Guidelines for Minimizing the Risk of Transmission of Agents Causing Spongiform Enecphalopathies via Medicinal Products, Draft No. 2, Biologicals 1992: pp. 155-158.

Dagalakis et al., Design of an artificial skin. Part III. Control of pore structure, J. Biomed. Matls. Res., vol. 14, 511-528 (1980).

Doillon, C.J. et al., Collagen-Based Wound Dressings: Control of the Pore Structure and Morphology, J. Biomed. Matls. Res., vol. 20, 1219-1228 (1986).

Doillon, C.J. et al., Collagen-Based Wound Dressing: Effects of Hyaluronic Acid and Fibronectin on Wound Healing, Biomaterials, vol. 7, pp. 3-8 (1986).

Doillon et al., Fibroblast & Epidermal Cell-Type I Collagen Interactions: Cell Culture and Human Studies, Scanning Microscopy, vol. 2, No. 2, pp. 985-992 (1988).

Doillon et al., Fibroblast—Collagen Sponge Interactions and the Spatial Deposition of Newly Synthesized Collagen Fibers in Vitro and in Vivo, Scannin Electron Microscopy, Part 3 , pp. 1313-1320 (1984).

Dubuisson & Kline, "Indications for peripheral nerve & brachial plexus surgery," Neurology of Trauma, vol. 10, No. 4, pp. 935-951 (1992).

Dufrane D., Cornu O., Schneider, Y.J.: "Physical and chemical procesing for a human dura mater substitute" Biomaterialsvol. 23, 2002, pp. 2979-2988, XP002443454.

Eismont et al., Treatment of dural tears associated with spinal surgery, J. Bone Joint Surg., vol. 63-A, No. 7, pp. 1132-1136 (1981).

Goldstein et al, Development of a reconstituted collagen tendon prosthesis, J. Bone Joint Surg., vol. 71-A, No. 8, pp. 1183-1191 (1989).

Gondo, G. et al, Peculiar computed tomographic images after intracrania use of microfibrillar collagen hemostat: report of three cases, Neurol. Surg., vol. 17, No. 11, pp. 1067-1071 (1989), abstract.

Hoffman et al., Septo-hippocampal regeneration through biosynthetic bridges containing adult Schwann cells, Soc. Neuro. Abs., vol. 18, Pt. 1, 271.1 (1992).

Jenq et al, Nerve Regeneration Changes with Filters of Different Pore Size, Experimental Neurology, vol. 97, pp. 662-671 (1987).

Keller et al., Repair of spinal dural defects with vicryl (polyglactin 910) mesh. J. Spinal Disorders, vol. 2, No. 2, pp. 87-92 (1989).

Krarup et al., "Factors that Influence Peripheral Nerve Regeneration: An Electrophysiological Study of the Monkey Median Nerve", Annals of Neurology, 2002, 51: 69-81.

Kuntz, R. and Saltzman, W., Neutrophil Motility in Extracellular Matrix Gels-: Mesh Size and Adhesion Affect Speed of Migration, Biophysical Journal, vol. 72, No. 3, pp. 1472-1480 (Mar. 1997).

Li et al, Semipermeable Collagen Nerve Conduits for Peripheral Nerve Regeneration, Polymeric Materials Science and Engineering, vol. 62, pp. 575-583 (1990).

Li, et al, The Development of Collagen Nerve Conduits that Promote Peripheral Nerve Regeneration, Biotechnology and Polymers (C. Gebelein ed.), 281-293 (1991).

Liu et al., A collagen-based sealant to prevent in vivo reformation of epidural scar adhesions in an adult rat laminectomy model, J. Neurosurg (Spine 1), vol. 97, pp. 69-74, 2002.

Madison, R. et al, Point Sources of Schwann Cells Result in Growth into a Nerve Ebtubulation Repair Site in the Absence of Axons: Effects of Freeze-Thawing, Experimental Neurology, vol. 128, pp. 266-275 (1994).

McGregor, D. et al, Avitene Granulomas of Colonic Serosa, Ann. Clin. Lab. Sci., vol. 16, No. 4, pp. 296-302 (1986).

Meddings, N. et al, Collagen Vicryl—A New Dural Prosthesis, Acta Neurochirurgica, vol. 117, pp. 53-58 (1992).

Nakajima, M. et al, An Intraperitoneal Tumorour Mass caused by Granulomas of Microfibrillar Collagen Hemostat (Avitene), Arch Pathol Lab Med., vol. 119:1161-1163 (1995).

Narotam et al., Collagen Matrix (Duragen) in Dural Repair: Analysis of a New Modified Technique, SPINE, vol. 29, No. 24, pp. 2861-2867 (2004).

Narotam et al., Collagen Matrix (Duragen) in spinal durotomy: technique appraisal and clinical results, The Spine Journal, vol. 3, pp. 147S-148S (2003).

Narotam et al., Operative Sepsis in Neurosurgery: A method of Classifying Surgical Cases, Neurosurg., vol. 34, No. 3, pp. 409-416 (Mar. 1994).

Nussbaum et al, Vicryl (polyglactin 910) mesh as a dural substitute in the presence of pia arachnoid injury, J. Neurosurg., vol. 71, No. 1, pp. 124-127 (Jul. 1989).

O'Neill, P., et al., Use of Porcine Dermis as a Dural Substitute in 72 Patients, J. Neurosurg., vol. 61, pp. 351-354 (1984).

Rabinowitz et al. "Growth of rat cortical neurons on DuraGen, a collagen=based dural graft matrix" Neurological Reasearch, 2005, vol. 27, pp. 887-894 XP008081483.

Public Health Issues Related to Animal and Human Spongiform Encephalopathies: Memorandum from a WHO Meeting, Bulletin of the World Health Org., vol. 70, Issue 2, pp. 183-190 (1992).

Saltzman et al, Antibody diffusion in human cervical mucus, Biophysical Journal, vol. 66, No. 2, pp. 508-515 (1994).

San-Galli et al, Experimental Evaluation of a Collagen-coated Vicryl Mesh as a Dural Substitute, Neurosurg., vol. 30, No. 3, pp. 396-401 (1992).

Schmidt et al, Chain Dynamics, Mesh Size, and Diffusive Transport in Networks of Polymerized Actin: a quasielectric light scattering and microfluorescence study, Macromolecules, vol. 22, No. 9, 3638-3649 (1989).

Sickmueller, B., Rubmann, D., BSE and Scrapie—German Federal Health Office (BGA) on Safety Measures to be Adopted for Medicinal Products, Drugs Made in Germany, vol. 37, Issue 2, pp. 36-49 (1994).

(56) References Cited

OTHER PUBLICATIONS

Taylor, D.M., Inactivation of the Unconventional Agents of Scrapie, Bovine Spongiform Encephalopathy and Creutzfeldt-Jakob Disease, J. Hosp. Infection, vol. 18 (Supplement A), pp. 141-146 (1991).

Tarlov, I., Structure of the nerve root, Arch. Neuro. Psych., vol. 37, No. 3, pp. 555-583 (1937).

Tsuruno, T., et al., An Arachnoid Plasty Technique Using a Collagen Seat and Fibrin Glue, JPN. J. Neurosurg., vol. 4, No. 2, pp. 193-195 (1995) (with translation & certificate of translation).

Visser C., Voute A., Costing J., Boon M., Kok L.: Microwave irradiation and cross-linking of collagen, Biomaterials, 1992, vol. 13, No. 1, pp. 34-37, XP002443453.

Wagner, W., Pachence, J., Ristich, J., Johnson, P., Comparative in Vitro Analysis of Topical Hemostatic Agents, J. Sur. Res., pp. 100-108 (1996).

Yamagata, S. et al, Clinical Experience with Expanded Polytetrafluoroethylene Sheet Used as an Artificial Dura Mater, Neuro Med Chir, vol. 33, pp. 582-585 (1993).

"Collagen Matrix, Inc., Launches DuraMatrixa Collagen Dura Substitute Membrane, Neuroflexa Flexible Collagen Nerve Cuff, and NeuroMatrixa Collagen Nerve Cuff" May 9, 2005, one page, XP002443455, Retrieved from the Internet: URL:http://www.collagenmatrix.com/PDF/05092005.pdf.

Archibald et al., "Long Term Maintenance of Axonal Regeneration in Primates Following Collagen Nerve Guide Repair of 2CMMedian Nerve Deficit", Society for Neuroscience Abstracts, 1992, vol. 18, Part1, Abstract.

Cox., "Transmissible Spongiform Encephalopathies—Literature Review: A Systematic Review of the Published Literature to Identify the Methods of Inactivation for Unconventional Agents of Transmissible Spongiform Encephalopathies", Medical Devices Agency, UK, 2001, pp. 1-13.

Extended European Search Report for Application No. 06253432.6 issued Nov. 28, 2008 (7 pages).

Extended European Search Report issued Jul. 30, 2007 for Application No. 06255056.1, dated Jul. 30, 2007 (11 pages).

Extended European Search Report issued Nov. 25, 2011 for Application No. 11175994.0 (5 pages).

Japanese Office Action issued May 10, 2011 for Application No. 2006-180095 (3 pages).

Japanese Office Action issued Jan. 31, 2012 for Application No. 2006-180095 (3 pages).

Kelly et al., Collagen Sponge Repair of Small Cerebrospinal Fluid Leaks Obviates Tissue Grafts and Cerebrospinal Fluid Diversion after Pituitary Surgery, Neurosurg., vol. 49, No. 4, pp. 885-890 (Oct. 2001).

Kline, D. And Hayes, G., The use of a resorbable wrapper for peripheral-nerve repair: Experimental studies in chimpanzees*. J. Neurosurg., vol. 21, No. 9, pp. 737-750 (Sep. 1964).

Kurze et al., Collagen sponge for surface brain protection. J. Neurosurg., vol. 43, No. 5, pp. 637-638 (1975).

Laun et al., Comparative study of lyophilized human dura mater and lyophilized bovine pericardium as dural substitutes in neurosurgery, Acta. Neurochirurgica, vol. 107: 16-21 (1990).

MacFarlane, M. and Symon, L., Lyophilised dura mater: experimental implantation and extended clinical neurosurgical use, J. Neur. Neursurg. Psych., vol. 42, No. 9, pp. 854-858 (1979).

Mamata et al, Microfibrillar collagen hemostat, Jpn J. Neurosurg., vol. 3, No. 4, pp. 354-359 (1994) [Japanese Language Reference] [English Abstract].

Wada, T. et al, A Foreign-body Granuloma due to Microfibrillar Collagen Hemostat Used during a Craniotomy: A Case Report, Jpn J. Neurosurg., vol. 3, No. 5, pp. 442-445 (1994) [Japanese Language Reference] [English Abstract].

Fig. 8

COLLAGEN DEVICE AND METHOD OF PREPARING THE SAME

CROSS-REFERENCE TO RELATED APPLICATIONS

This application is a continuation of U.S. patent application Ser. No. 11/171,638, filed on Jun. 30, 2005, entitled "Collagen Device and Method of Preparing the Same," which is a continuation-in part-of U.S. patent application Ser. No. 10/955,835, filed Sep. 30, 2004, entitled "Collagen Device and Method of Preparing the Same," which claims priority to previously filed provisional applications U.S. Ser. No. 60/542,968, filed Feb. 9, 2004, entitled "Collagen and Method of Preparing the Same," and Ser. No. 60/565,747, filed Apr. 27, 2004, entitled "Collagen Device and Method of Preparing the Same," all of which are hereby incorporated herein by reference in their entirety.

STATEMENT REGARDING FEDERALLY SPONSORED RESEARCH

Not Applicable.

FIELD OF THE INVENTION

The present invention relates to a collagen device and a method of preparing the same. More specifically, the present invention relates to a method for preparing a collagen device for use as an implant to replace, reinforce or strengthen bodily tissue, an adhesion barrier, or for use as a short-term body contact for moisture retention, hemostasis or tissue protection.

BACKGROUND OF THE INVENTION

The human brain and spinal cord are covered with meningeal membranes whose integrity is critical to the operation of the central nervous system. When the integrity of a person's meningeal membranes is intentionally or accidentally compromised, serious consequences may ensue, unless the membranes can be repaired. The meningeal membrane comprises three overlapping layers of tissue, which are in order from outside to inside, the dura mater (or dura), the arachnoid and the pia mater. Repairing damaged meningeal membranes has largely focused on implantable and/or resorbable constructs (known as dural substitutes) which are grafted to the damaged dura mater and are designed to replace and/or regenerate the damaged tissue.

Conventional dural substitutes are categorized as either onlay (e.g., sutureless) grafts or as suturable grafts. The onlay grafts overlap and contact the dura mater when covering an area of damaged dura mater. With such contact, the onlay grafts substantially conform to a geometry or general curvature of the meningeal membrane and/or brain. The weight of the onlay graft itself holds the graft in place to maintain the positioning of the graft relative to the tissue. Suturable dural grafts cover an area of damaged dura mater and attach to the meningeal membranes using sutures to maintain the graft in place.

SUMMARY OF THE INVENTION

The present invention is directed to a collagen device that has a plurality of pores wherein a majority of the pores have a diameter of less than 10 µm. Surprisingly, the collagen device made in accordance with the present invention has good handling properties, as the collagen device is sufficiently flexible to conform to irregular-shaped surfaces but stiff enough that it does not curl or adhere to itself, instruments or the practitioner's gloved hands when wet. In addition, the collagen device in accordance with the present invention has very good strength properties, such as tensile strength, making it very easy to handle for the physician. Further, the collagen device in accordance with the present invention can be made the same shape or size as conventional collagen devices, such as currently available collagen dural grafts, while still providing the surgeon with a device that has superior strength and handling properties.

The collagen device made in accordance with the present invention is substantially fully resorbable, despite having a majority of its pores having a diameter of less than 10 µm. Surprisingly, the present inventors have found that despite the fact that those skilled in the art believe that the pore size must be sufficiently large enough (150 µm pore diameter is preferred for internal pores and 70 µm is preferred for surface pores) to permit growing meningeal tissue to infiltrate therein, the present invention collagen is replaced by growing meningeal tissue and is substantially fully resorbable even though a majority of its pores have a diameter of less than 10 µm. In accordance with an exemplary embodiment of the present invention, a collagen device is prepared by mixing collagen with purified water for a period of time sufficient to form a mixture. The pH of the mixture is adjusted to a pH level sufficient to substantially solubilize the collagen. A first predetermined amount of the mixture is placed into a container. The mixture is subject to a lyophilizing process and formed into a collagen device. The collagen device is also cross-linked. The collagen device has a plurality of pores wherein a majority of the pores have a diameter of less than 10 µm. To use the collagen device as an implant to replace, reinforce or strengthen bodily tissue, or to act as an adhesion barrier, the collagen device is placed in contact with bodily tissue and that contact is maintained until the collagen device is substantially resorbed within the bodily tissue.

In one embodiment, a dural graft includes a collagen layer having substantially planar opposed surfaces and at least one reinforcement layer disposed on at least one planar surface of the collagen layer. Both the collagen layer and the reinforcement layer are configured to substantially conform to a curvature of a tissue. The reinforcement layer has a suture retention strength that is greater than a suture retention strength of the collagen layer. The present dural graft, therefore, is configured for use as both an onlay graft and a suturable graft. Because the dural graft substantially conforms to a curved tissue surface, the dural graft minimizes the presence of gaps between the dural graft and the tissue. Additionally, the dural graft can withstand a suture pull out stress either while the dural graft is sutured to a tissue or after the dural graft has been sutured to the tissue.

BRIEF DESCRIPTION OF THE DRAWINGS

The invention can be more fully understood from the following detailed description taken in conjunction with the accompanying drawings, in which.

DETAILED DESCRIPTION OF THE INVENTION

It will be understood that the foregoing is only illustrative of the principles of the invention, and that various modifications can be made by those skilled in the art without departing from the scope and spirit of the invention. All references cited herein are expressly incorporated by reference in their entirety.

A collagen device in accordance with the present invention is prepared by mixing collagen with purified water for a period of time sufficient to form a mixture. The ratio of collagen to purified water is between approximately 0.4% to 5.0% w/w. The pH of the mixture is then adjusted to a pH level sufficient to substantially solubilize the collagen. A predetermined amount of the mixture is then placed into a container. The mixture is then formed into a collagen sheet by a lyophilizing process. The mixture could also be formed into a block, cylinder, or other desired shape, which will hereinafter be referred to collectively as a collagen sheet. The collagen sheet is then cross-linked. During the cross-linking, the collagen sheet is preferably exposed to a liquid or vapor form of a cross-linking agent, such as formaldehyde or glutaraldehyde. Thereafter, the collagen sheet is ventilated if the cross-linking agent is vapor or relyophilized if it is liquid. The steps of forming the mixture into a collagen sheet and the cross-linking could be reversed.

The resulting collagen sheet has a plurality of pores wherein a majority of the pores have a diameter of less than 10 μm. Preferably, greater than 80% of the pores have a diameter of less than 10 μm. More preferably, greater than 90% of the pores have a diameter of less than 10 μm. Even more preferably, greater than 95% of the pores have a diameter of less than 10 μm. Yet even more preferably, greater than 98% of the pores have a diameter of less than 10 μm. And even more preferably, approximately all of the pores have a diameter of less than 10 μm.

Figure 1A:
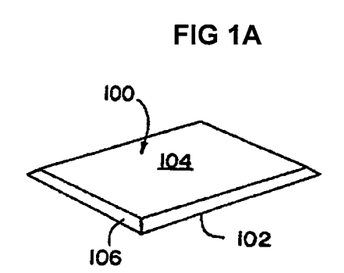
FIGS. 1A, 1B, and 1C are a lower perspective view, side view and top view, respectively, of a collagen device.
Figure 1B:
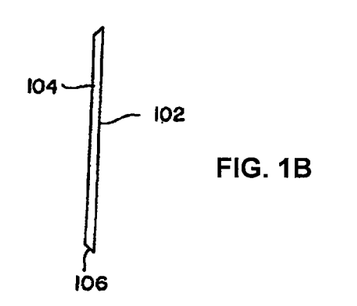
Figure 1C:
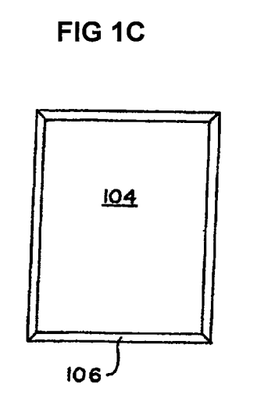

The collagen sheet 100 may be cut into predetermined shapes or formed in predetermined shapes that are formed to size. Sheet 100 has a top surface 102, bottom surface 104 and peripheral edge 106. The edge 106 of each predetermined shape may be chamfered to allow a smooth profile of the edge when it is wetted in situ, as shown in FIGS. 1A-1C. The angle of the chamfer D is preferably approximately 30 to 75 degrees from vertical pivoting from the top or bottom surface.

In an alternate embodiment, before cross-linking, the collagen sheet can be compressed by rollers. The collagen sheet can be compressed to between approximately one-half to one-eighths the original thickness C of the collagen sheet.

In use, for use as a dural substitute or adhesion barrier, or for short-term body contact for moisture retention, hemostasis, or tissue protection, the collagen sheet may be placed in contact with bodily tissue. When used as an implant, contact between the collagen sheet and the bodily tissue is maintained. In time, currently estimated to be about nine (9) months, the collagen sheet will be fully resorbed. When placing the collagen sheet in contact with bodily tissue, the collagen sheet does not stick to or adhere to instruments, including the surgeon's hands. Also, should the collagen sheet need to be repositioned, the surgeon is able to do so without the collagen sheet breaking apart.

The collagen sheet has very good strength properties, such as tensile strength, making it very easy to handle for the physician. In testing done in accordance with ASTM 638, Type V, the collagen sheet in accordance with the present invention had an average tensile strength greater than 6.0 psi, ranging from 7.43 psi to 9.76 psi per lot, with an average of about 8.74 psi for all lots tested. Currently available collagen sheets were tested and they had an average tensile strength of about 6.00 psi.

One skilled in the art will readily recognize that the collagen device described herein can also be used to deliver biologically active agents such as, for example, growth factors, autologous cells, bone marrow, antibiotics, anti-cancer agents, and gene and DNA constructs.

Figure 2:
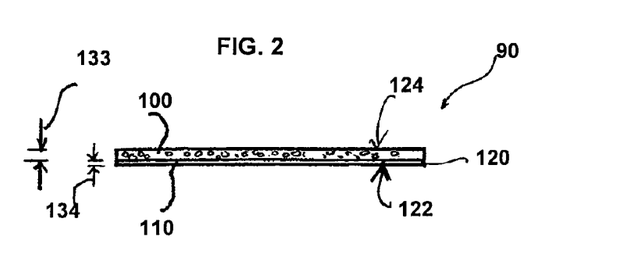
FIG. 2 is a collagen device having a reinforcement layer laminated thereto, according to one aspect of the invention.
Figures 7A, 7B:
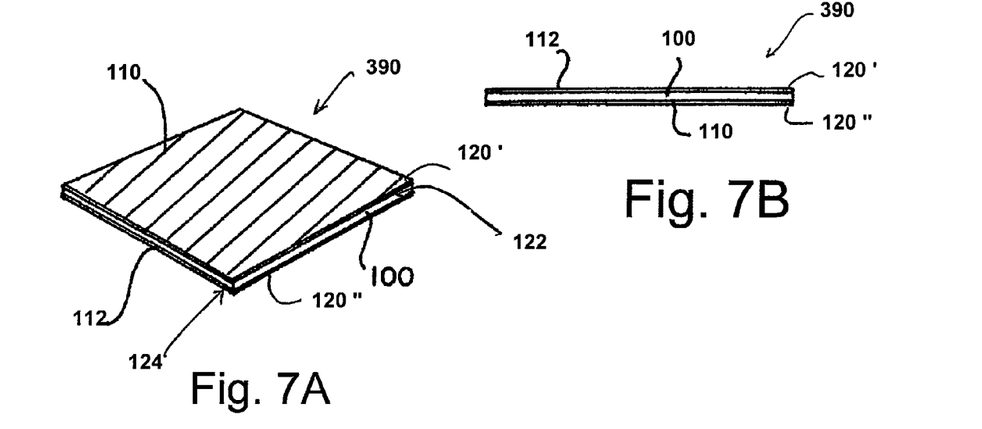
FIGS. 7A-7B show a further embodiment of a multi-layered collagen device.

The collagen device and method of preparing the same may be used to provide a component of a multi-layer or laminate product, as illustrated in FIGS. 2, 7A, and 7B. The collagen sheet 100 can include one or more layers or laminates 110, 112 as shown (FIG. 2 shows one laminate, and FIGS. 7A and 7B show two laminates). The collagen sheet described can be laminated or otherwise attached with one or a number of the following: film, felt, woven or non-woven matrix, mesh or a second collagen sheet. For example, a collagen sheet as described may be combined with an impermeable film to provide a watertight construct. The final multi-layer construct would be manufactured in order to improve one or a number of the following characteristics: suture retention strength, fluid impermeability, resorption duration, handling characteristics, stiffness, and/or adhesion properties to tissues.

The collagen sheet may include a layer of a film or woven matrix at the time of processing the collagen sheet so that it is incorporated within the boundaries of the collagen sheet. An alternate method would be to apply the second layer to the collagen sheet by various methods including but not limited to adhesives, heat-pressing, heating in an oven with or without a vacuum, exposing the material to heating elements or heated air, and combining layers during partial processing of one or both materials. The laminate or multi-layer product can include any biocompatible materials that may or may not be resorbable. In addition, the layer added to the collagen device may have biological active agents (e.g., antibiotics, growth factors, hemostasis factors, anti-adhesion agents, anti-cancer agents) incorporated within or upon the material while it may or may not be on the collagen device.

The various dimensions of the laminate structures may vary from matching dimensions to one or multiple layers have greater or smaller dimensions than one of the other layers. In this manner, the preferential characteristics of one layer may be emphasized at a certain location as desired, depending upon the requirements of the surgical procedure.

A laminated, bioimplantable dural graft 90 product is further illustrated in FIGS. 2-7B. The dural graft 90, which is biocompatible, is configured for use as both an onlay graft and a suturable graft. The laminated dural graft product 90, when hydrated, is sufficiently pliable so as to sufficiently conform to a curvature of a tissue surface to which it is applied. In one embodiment, the dural graft 90 has sufficient pliability to allow it to conform to the curved surface of a meningeal membrane. As noted above, the use of a laminated graft product can have improved properties, including suture retention strength and fluid impermeability.

FIG. 2 illustrates one embodiment of a laminated dural graft 90 having a collagen layer 100 and a reinforcement layer 120. The collagen layer 100, such as described above with respect to FIGS. 1A-1C, is formed as a sheet having a first planar surface 122 and an opposed second planar surface 124. The collagen layer 100 is configured to substantially conform to a curved tissue surface. For example, the collagen layer 100 defines a substantially porous structure that, in part, provides the collagen layer 100 with a level of compliance that allows the collagen layer 100 to substantially conform to or follow a general geometry or curvature of a tissue surface.

The reinforcement layer 120 can be a biocompatible sheet or film that enhances certain properties (e.g., suture retention strength, fluid impermeability) of the collagen layer 100, if used alone, while still maintaining the ability of the laminated graft 90 to conform to a surface to which it is applied. For example, the reinforcement layer 120 can be formed from a fluoropolymer, such as GORTEX, to preserve a desired level of compliance of the dural graft 90. In another example, the reinforcement layer 120 can be formed of a bioabsorbable film, such as polylactic acid (PLA), polyglycolic acid (PGA), polycaprolactone (PCL), polydioxanone (PDO), trimethylene carbonate (TMC), copolymers or blends thereof. The thickness of the reinforcement layer 120, when formed from the bioabsorbable film, along with the thickness of the collagen layer 100, affects the overall conformability of the dural graft 90. For example, the collagen layer 100 has a thickness 133 in the range of approximately 0.02 inches to 0.20 inches. To maintain the conformability of the dural graft 90, the bioabsorbable reinforcement layer 120 has a thickness 134 in the range of approximately 0.001 inches to 0.016 inches. When combined, the collagen layer 100 and the reinforcement layer 120 produce a conformable dural graft 90 having a thickness in the range of approximately 0.021 inches to 0.216 inches.

As shown in FIG. 2, the reinforcement layer 120 is positioned adjacent to the first planar surface 124 of the collagen layer 100. The reinforcement layer 120 can be combined with the collagen layer 100 in a variety of ways. For example, the two layers 100, 120 can be physically combined or they can simply be placed adjacent each other.

Examples of techniques for physically joining the reinforcement layer 120 and the collagen layer 100 include heat pressing, heating, such as in an oven, with or without a vacuum, exposing the material to heating elements or heated air, or ultrasonically spot welding the reinforcement layer 120 to the planar surface 124 of the collagen layer 100. These procedures melt a portion of the reinforcement layer 120 to the collagen layer 100 to secure the reinforcement layer 120 to the collagen layer 100 and minimize relative displacement or shifting of the reinforcement layer 120 relative to the collagen layer 100 after implantation. The reinforcement 120 layer may be introduced to the collagen during the processing of the collagen material. The reinforcement layer 120 may be placed on top or between layer(s) of collagen mixture prior to final processing (e.g., lyophilization).

Figure 4:
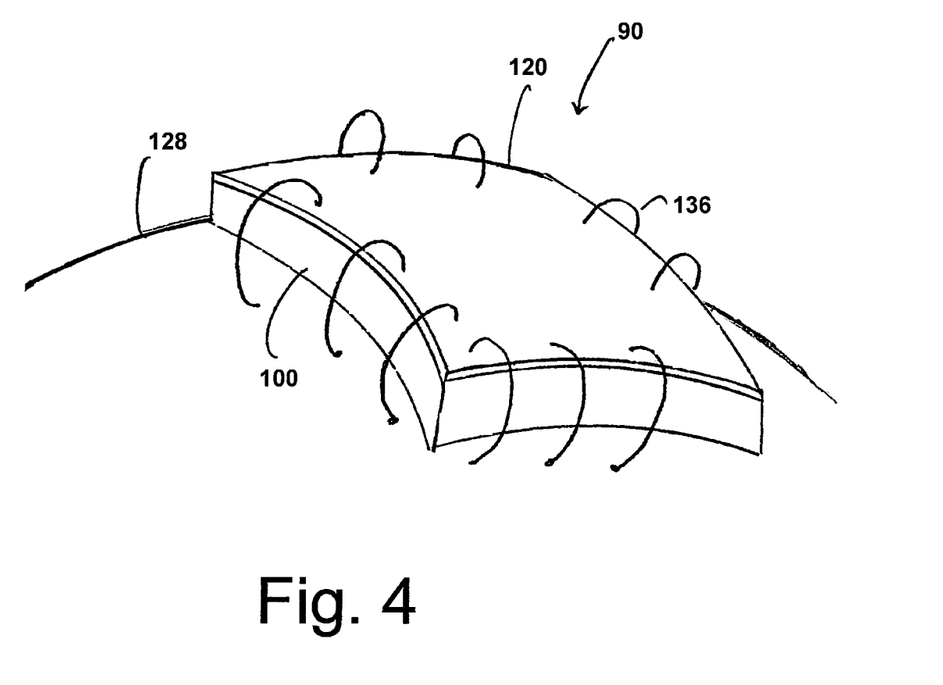
FIG. 4 is a perspective view of the implanted collagen device of FIG. 3.

As noted above, the reinforcement layer 120 need not be physically coupled or attached to the collagen layer 100 prior to implantation of the dural graft 90. Instead, the surface tension of a body fluid (e.g., cerebral spinal fluid) in contact with the dural graft 90 maintains contact between the reinforcement layer 120 and the collagen layer 100 during implantation. In one embodiment, the reinforcement layer 120 and the collagen layer 100 can be physically joined together after implantation. For example, when the dural graft 90 attaches to a meningeal membrane, sutures are applied about the perimeter of the graft 90, such as illustrated in FIG. 4. While the sutures attach the dural graft 90 to the meningeal membrane, the sutures also physically couple the separate, non-attached reinforcement layer 120 and the collagen layer 100.

As noted above, the reinforcement layer 120 can enhance certain properties of the collagen layer 100, such as the suture retention strength of the collagen layer 100. In one example the reinforcement layer 120 has a suture retention strength greater than that of the collagen layer 100. This feature increases the tear resistance of the dural graft 90, either while the dural graft 90 is sutured to a tissue or after the dural graft has been sutured to the tissue, and enables the laminated graft product 90 to be less susceptible to suture pull-out. For example, the suture retention strength of the collagen layer 100 alone is approximately 0.07 pounds force. The reinforcement layer 120 increases the suture retention strength of the collagen layer 100 such that the suture retention strength for the dural graft 90 (e.g., the combination of the reinforcement layer 120 and the collagen layer 100) is in the range of approximately 2 pounds force and 4 pounds force, for example. The reinforcement layer 120 in combination with the collagen layer, therefore, allows secure suturing of the dural graft 90 to a meningeal membrane 128 to maintain the relative position of the dural graft 90 relative to the meningeal membrane 128 while minimizing the ability for the suture to inadvertently tear, pull-out from, or become extracted from the dural graft 90.

As indicated above, the collagen layer 100 defines a substantially porous, sponge-like structure that resists the passage of fluid, such as cerebrospinal spinal fluid (CSF), from the brain 132. The collagen layer 100, however, is not fluid impervious. In one embodiment, the reinforcement layer 120 is substantially fluid impermeable and provides a level of fluid impermeability to the dural graft 90. For example, reinforcement layer 120 can be formed as a film of polylactic acid (PLA), polydioxanone (PDO), or other materials as noted above. Such materials limit the passage of fluids, such as CSF. When used in conjunction with the collagen layer 100, the fluid impermeable reinforcement layer 120 limits or minimizes the flow of CSF from the brain 132 and past the collagen layer 100.

Figure 3:
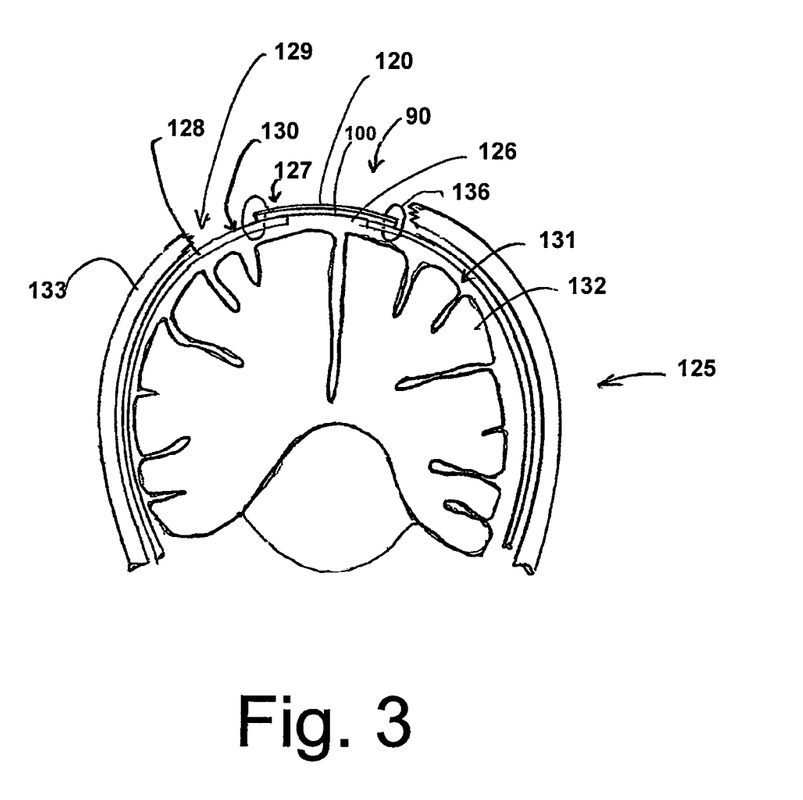
FIG. 3 is a sectional view of a portion of a cranium having the collagen device of FIG. 2 implanted therein.

The dural graft 90 can be utilized during a surgical procedure to repair or replace damaged meningeal membranes. FIGS. 3 and 4 illustrate examples of the positioning and coupling of the dural graft 90 to a meningeal membrane during a surgical procedure. FIG. 3 illustrates a portion of a cranium 125 having a damaged dura mater site 126. During implantation, the dural graft 90 is inserted through an opening 129 of the skull 133 of the cranium 125 and is placed in contact with a meningeal membrane 128 at the site 126. For example, the dural graft 90 is placed at the site 126 such that an edge 127 of the dural graft 90 overlaps a portion of the meningeal membrane 128 and contacts a non-damaged portion of the dura mater 130.

As the dural graft 90 contacts the dura mater 130, the dural graft 90 (e.g., the hydrated dural graft) substantially conforms to a general curvature of the meningeal membrane 128. For example, as shown in FIGS. 3 and 4, both the collagen layer 100 and the reinforcement layer 120 of the dural graft 90 form a curved shape substantially similar to a curvature of the meningeal membrane 128. The conformance of the dural graft 90 minimizes the presence of gaps between the dural graft 90 and the meningeal membrane 128 thereby allowing the dural graft to substantially contain CSF 131 within the brain 132 after implantation of the graft 90.

With the graft having a characteristic of conformability, the dural graft 90 can be used as an onlay graft that does not require sutures to secure the dural graft 90 to the meningeal membrane 128. As such, the weight of the dural graft 90 maintains the relative positioning of the dural graft 90 relative to the site 126. In another embodiment, the dural graft 90 can be secured to the meningeal membrane 128 using sutures 136. As illustrated in FIG. 4, one or more sutures 136 are inserted through the dural graft 90 and through the meningeal membrane 128 about the edge or perimeter 127 of the dural graft 90. The presence of the reinforcement layer 120, as part of the dural graft 90, increases the suture retention strength of the collagen layer 100 and minimizes the ability for the sutures 136 to be inadvertently torn or pulled out from the collagen layer 100.

Once the dural graft 90 has been implanted at a site 126, the collagen layer 100 resists the formation of adhesions with the surrounding tissues. Therefore, relative to the meningeal membrane, the orientation of the dural graft 90 can be selected to minimize adhesions between the dural graft 90 and portions of the surrounding tissue. For example, as shown in FIG. 3, the collagen layer 100 of the dural graft 90 is oriented toward the meningeal membrane 128 and opposite to the skull 133. With such an orientation, the collagen layer 100 of the dural graft 90 limits or resists the formation of adhesions with the meningeal membrane 128. Alternately, if one orients the dural graft 90 such that the reinforcement layer 120 contacts the meningeal membrane 128, the risk of the formation of adhesions between the collagen layer 100 and the skull 133 is reduced.

Figure 5:
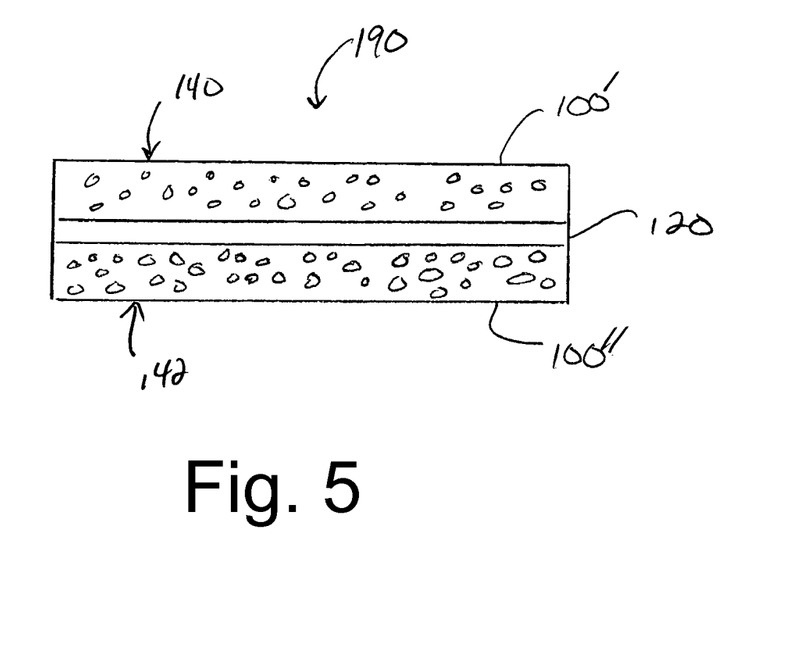
FIG. 5 is a multi-layered embodiment of a collagen device.

One skilled in the art will appreciate that a laminated dural graft product 190 can be constructed in a variety of ways. In one construction, as shown in FIG. 5, the dural graft 190 includes two separate collagen layers: a first collagen layer 100' and a second collagen layer 100" with the reinforcement layer 120 disposed between layers 100', 100". In this configuration, the dural graft 90 has two available planar collagen surfaces 140, 142 that can contact tissue at a surgical site. After implantation of the dural graft 190 at a site 126, such as illustrated in FIG. 3, both surfaces 140, 142 of the collagen layers 100', 100" limit or resist the formation of adhesions between the dural graft 190 and the surrounding tissue (e.g., the meningeal membranes 128 or the skull 133).

Figure 6:
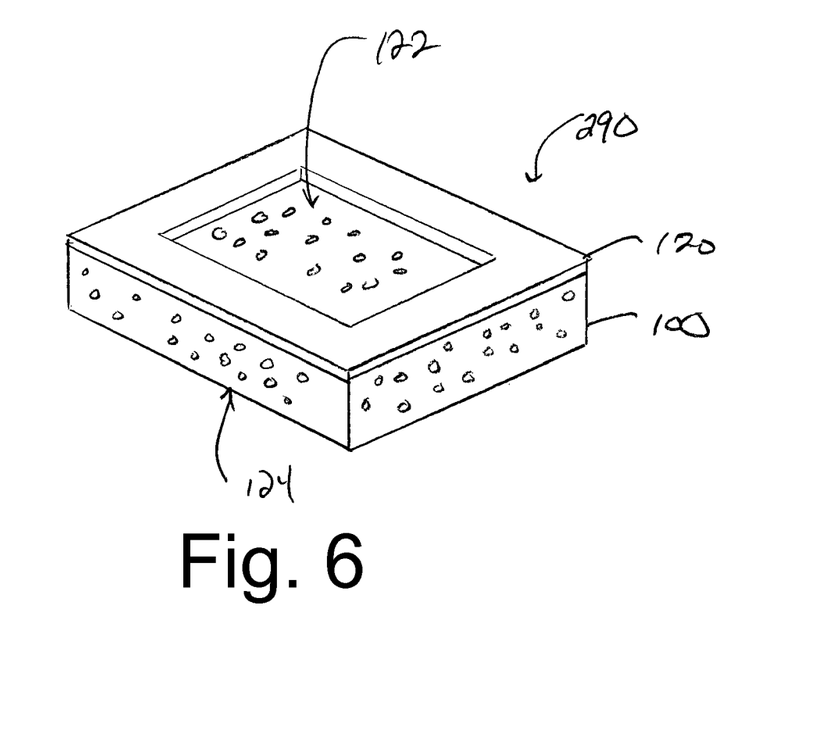
FIG. 6 is another embodiment of a multi-layered collagen device.

In an embodiment, as shown in FIG. 6, a dural graft 290 has the reinforcement layer 120 disposed on a planar surface 122 of the collagen layer 100 and positioned around a perimeter or edge 127 of the collagen layer 100. In this embodiment, the dural graft 290 has two available planar collagen surfaces 122, 124 that can contact tissue at a surgical site. After implantation of the dural graft 290 at the site, both surfaces 122, 124 of the collagen layer 100 100" limit or resist the formation of adhesions between the dural graft 290 and the surrounding tissue (e.g., the meningeal membranes 128 or the skull 133).

In yet another embodiment, as shown in FIGS. 7A and 7B, a dural graft 390 includes the collagen layer 100 having a first reinforcement layer 120' disposed on the first planar surface 122 of the collagen layer 100 and a second reinforcement layer 120" disposed on the second planar surface of the collagen layer 100. In one exemplary embodiment, the first 120' and second 120" reinforcement layers are formed from a thin, perforation-containing polymeric sheet. Examples of suitable polymeric sheets include blends or copolymers of polylactic acid (PLA), polyglycolic acid (PGA), polycaprolactone (PCL), and polydioxanone (PDO). The pores or perforations are believed to be useful in that they enable tissue ingrowth.

EXAMPLE

Figure 8:
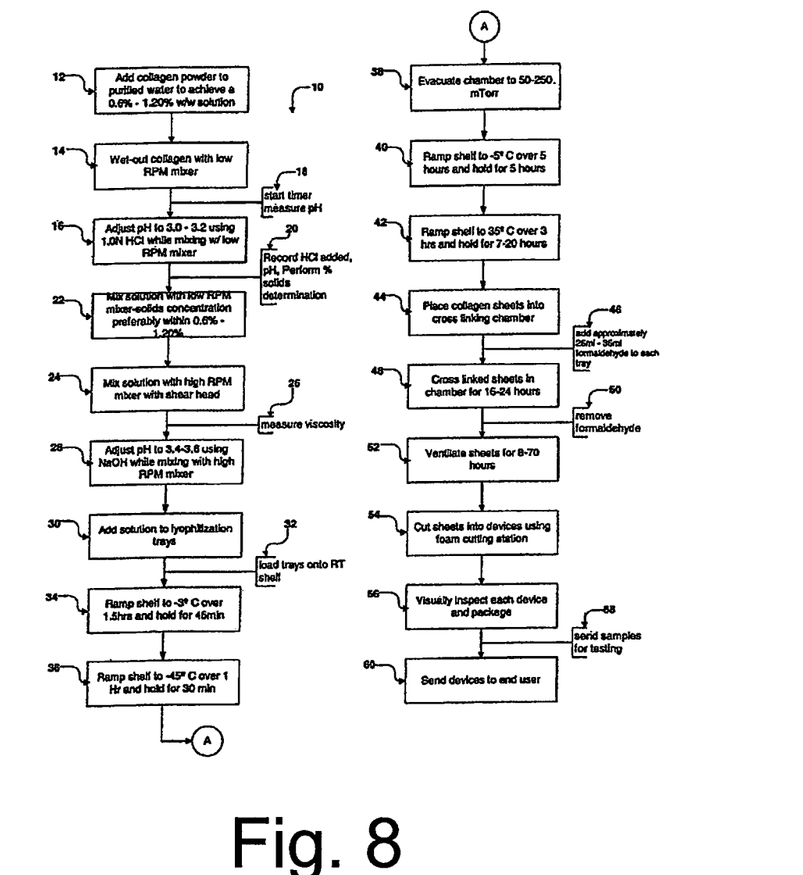
FIG. 8 is a flow chart illustrating a method of preparing a collagen device in accordance with the present invention.

Referring now to FIG. 8, a non-limiting example of a collagen device made in accordance with method 10 for preparing a collagen device in accordance with the present invention is illustrated. The method includes a first step 12 of adding a collagen powder to purified water preferably in a ratio of approximately 0.4% to 5.0% w/w of collagen powder to purified water to hydrate the collagen powder. A ratio of about 0.40% to about 3.50% w/w is even more preferred. While a ratio of about 0.60% to about 1.20% w/w is most preferred. The collagen powder is commercially available from Datascope of 14 Phillips Parkway, Montvale, N.J.

The hydrated collagen is then mixed in step 14 with the purified water for a period of time sufficient to form a mixture. In an exemplary embodiment, this period of time is preferably from about three (3) to six (6) minutes. The mixing is preferably achieved first with a relatively gentle mixer sufficient to solubilize the collagen with minimal or no shearing of the collagen fibers. This gentle mixer may be a Lightnin™ mixer model L1U03 that mixes at 0 to 1000 rpm and is commercially available from Lightnin, which is a unit of General Signal of Coolock Dublin, Ireland.

During the mixing, the pH of the mixture is adjusted to a predetermined pH level in step 16. In one embodiment, the predetermined pH level is preferably between approximately 1.5 and 4.0, which is below the isoelectric point of the mixture. In another embodiment, the predetermined pH level is preferably between approximately 11.0 and 13.5, which is above the isoelectric point of the mixture. At the initiation of the adjusting of the pH, a timer is initiated, as illustrated in step 18. The pH of the mixture is preferably achieved while the mixture is being mixed with the gentle mixer at a mixing speed of between about 400 and 1000 rpm to a pH of about 3.0-3.2. To adjust the pH, 1.0N HCl is preferably added to the mixture. Of course, while hydrochloric acid is preferably used to adjust the pH of the mixture, other acids may be used, such as, for example, acetic acid, lactic acid, or phosphoric acid.

The adjusting the pH step is preferably achieved without overshooting the predetermined pH level. If one were to overshoot the pH level, then an additive such as NaOH would have to be added to the mixture to raise the pH level. Sodium hydroxide is preferably used to adjust the pH of the collagen solution, although other hydroxides may be used, such as, for example, other alkali metal hydroxides or ammonium hydroxides. But the present inventors have discovered that the raising and lowering or lowering and raising of the pH of the mixture may cause inconsistent freezing which may affect the desired pore size and biocompatibility due to the change in ionic strength. Thus, it is preferred not to overshoot the predetermined pH level. During the adjusting step 16, the amount of HCl added to the mixture, the pH, and a calculation of the percentage of the solids concentration is determined, as illustrated in step 20.

Once the predetermined pH level is achieved in step 16, the mixture is continued to be mixed with the gentle mixer for preferably at least one (1) hour total elapsed time from the time the powder was added to the purified water in step 12, as illustrated in step 22. The percentage of solids concentration is preferably within 0.6%-1.2%.

After mixing with the gentle mixer, the mixture is mixed with a shear mixer preferably at a mixing speed of between about 8000 and 9000 rpm, as illustrated in step 24. The shear mixture preferably operates at a speed that is sufficient to mechanically break down the collagen powder. This shear mixer may be a Silverson™ mixer that mixes at 0 to 10,000 rpm and is commercially available from Silverson Machines Limited of Waterside Chesham Bucks, England. The pH of the mixture is preferably further adjusted while the mixture is being mixed with the shear mixer to a pH of about 3.4-3.6.

The viscosity of the mixture is measured in step 26 preferably with the initiation of mixing step 24.

The pH is raised to improve sheet handling properties. This adjustment is preferably achieved without overshooting the predetermined pH level. If one were to overshoot the pH level, then an additive such as HCl would have to be added to the mixture to lower the pH level.

Once step 28 is complete, a predetermined amount of the mixture is placed into a container, as illustrated in step 30. A sufficient amount of the mixture is placed into the container so that the resultant collagen device will have sufficient thickness to perform as a dural substitute, adhesion barrier, or for short-term body contact for moisture retention, hemostasis, or tissue protection. The tray is preferably made of a plastic material, such as PETG. However, the trays could be made from glass, metal, ceramic, a base material coated with a non-stick surface such as TEFLON® or polished metal. The trays could also be shaped with individual compartments with each compartment shaped to the desired final form of the collagen device. For example, the compartments can be of 1"×1" square, with beveled edges on each edge. Of course, many different sizes or shapes could be made with or without beveled edges, including within the same tray, to meet the needs of the surgeon.

The container is placed in a chamber, as illustrated in step 32. In a currently preferred embodiment, the container is placed on a shelf within the chamber, and the shelf has a temperature control mechanism to control the temperature of the shelf, and thereby the chamber. Hereinafter, the temperature of the chamber will be referred to, but one skilled in the art will recognize that this includes the temperature of the shelf. The temperature control mechanism is regulated so that the temperature of the chamber is preferably above the crystallization temperature of the mixture. The bottom surface of the container is preferably planer to mate with the planer surface of the top surface of the shelf.

In one embodiment, the temperature of the chamber can be at room temperature, which is between about 15 to 25° C. In another embodiment, the chamber can be about −3° C. In yet another embodiment, the chamber temperature can be set well below the crystallization temperature of the mixture to about −50° C. to deep freeze the mixture upon placement into the chamber. If the temperature is at room temperature, then the temperature of the chamber is adjusted to a second predetermined temperature approximately slightly above the crystallization temperature of the mixture over approximately a first predetermined time period, as illustrated in step 34. Preferably, the second predetermined temperature is −3° C. to −5° C., and the first predetermined time period is approximately sixty (60) minutes. The chamber is then held at the second predetermined temperature for approximately forty-five (45) minutes.

The temperature of the chamber is the cooled to approximately −45° C. over a period of approximately one (1) hour, as illustrated in step 36. The chamber is preferably held at this approximate temperature for about at least thirty (30) minutes.

A vacuum is then pulled in the chamber to approximately a first predetermined level sufficient to allow adequate sublimation of ice crystals the chamber is evacuated, as illustrated in step 38. The vacuum can be pulled while the temperature of the chamber is being held at −45° C. in step 34. In a currently preferred exemplary embodiment, the chamber is evacuated to about 50-250 mTorr. Sublimation of the ice crystals results in the formation of a collagen sheet having a plurality of pores wherein a majority of the pores have a diameter of less than 10 μm.

The chamber temperature is then raised to a sufficient temperature and held at this temperature for a sufficient period of time until primary drying occurs in the mixture, as illustrated in step 40. In a currently preferred exemplary embodiment, the chamber is ramped up to about −5° C. over about five (5) hours and this temperature is maintained for about five (5) hours. In this non-limiting Example, the mixture is transformed by the above steps into a collagen sheet.

As illustrated in step 42, the temperature of the chamber is then changed to approximately room temperature over approximately seven (7) hours. In a currently preferred exemplary embodiment, the chamber is raised to about 35° C. over approximately three (3) hours and is held at this temperature for a sufficient period of time until secondary drying occurs in the collagen sheet without excessive drying or meltback, which in a currently preferred embodiment is for about seven (7) to twenty (20) hours.

In an alternate embodiment, the collagen sheet could be compressed by rollers or plates, as one skilled in the art will readily recognize. The rollers can compress the sheet to between one-half to less than 5% of the sheets original thickness. Compressing the sheet may result in a collagen sheet that is stronger than conventional sheets.

The collagen sheet is then placed in a cross-linking chamber, as illustrated in step 44. The sheets of collagen can be hung in the cross-linking chamber or placed on screens. Of course, the sheets could remain in the same chamber, and the cross-linking processing could take place in this chamber.

A predetermined amount of a cross-linking agent is added to the cross-linking chamber in step 46. The predetermined amount of formaldehyde is sufficient to at least partially saturate the collagen sheet. In a currently preferred exemplary embodiment, the cross-linking agent is formaldehyde, and the predetermined amount of formaldehyde is between approximately 25 ml and 35 ml. (Of course, the amount of formaldehyde added is dependent on the number of sheets and size of the chambers). The collagen sheet is exposed to a liquid or vapor form of the cross-linking agent. The cross-linking agent is removed from the cross-linking chamber after approximately sixteen (16) and twenty-four (24) hours in steps 48 and 50.

The collagen sheet is preferably cross-linked by vapor cross-linking or solution cross-linking. If a solution is used, the sheet is preferably dehydrated by lyophilization. Cross-linking agents such as formaldehyde, glutaraldehyde, carbodiimides or difunctional succinimides may be used. Alternatively, the matrix may be cross-linked by dehydrothermal cross-linking or UV radiation.

The collagen sheets are ventilated for between approximately eight (8) and seventy (70) hours in step 52, to remove excess cross-linking agent. Where it is desirable to include a reinforcement layer 120, this layer can be applied to the collagen sheet after step 52. In one embodiment, if physical joinder of layer 120 and the collagen layer is desired, this can be affected using heat pressing, heating in an oven with or without a vacuum, exposing the material to heating elements or heated air, or ultrasonic spot welding.

The collagen sheet is then cut into the desired shapes at a cutting station in step 54. The collagen sheet may be formed in predetermined shapes that are formed to size within the tray. The edge of each predetermined shape may be chamfered to allow a smooth profile of the edge when it is wetted in situ. The angle of the chamfer is preferably approximately 30 to 75 degrees from vertical.

Each cut section of the collagen sheet is then inspected, preferably visually, in step 56. Thereafter, some samples can be sent for testing in step 58 and the remaining cut sections can be packaged in a conventional manner sterilized and then sent to the end user, in step 60. The collagen sheet is tested, preferably by test method ASTM E1294, to ensure that the porosity of the sheet is less than 10 µm in step 58.

The steps of cutting the collagen sheet into the desired shapes and the cross-linking could be reversed.

One skilled in the art will appreciate further features and advantages of the invention based on the above-described embodiments. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. Accordingly, the invention is not to be limited by what has been particularly shown and described, except as indicated by the appended claims. All publications and references cited herein are expressly incorporated herein by reference in their entirety.

What is claimed is:

1. A bioimplantable dural graft material comprising:
   a collagen layer having planar opposed surfaces and having a plurality of pores, wherein a majority of the pores have a diameter of less than 10 micrometers; and
   at least one reinforcement layer disposed on at least one planar surface of the collagen layer, the reinforcement layer having a suture retention strength greater than a suture retention strength of the collagen layer wherein a combination of the reinforcement layer and collagen layer provides a suture retention strength in the range of about 2 pounds force to 4 pounds force, the reinforcement layer further being configured to conform to a curvature of a tissue.

2. The bioimplantable dural graft material of claim 1, wherein the reinforcement layer comprises a substantially fluid impermeable material.

3. The bioimplantable dural graft material of claim 1, wherein the reinforcement layer is formed from a bioabsorbable polymer.

4. The bioimplantable dural graft material of claim 3, wherein the bioabsorbable polymer is selected from the group consisting of polylactic acid, polyglycolic acid, polycaprolactone, polydioxanone, trimethylene carbonate, copolymers or blends thereof.

5. The bioimplantable dural graft material of claim 1, wherein the reinforcement layer couples to at least one planar surface of the collagen layer.

6. The bioimplantable dural graft material of claim 5, wherein the reinforcement layer physically couples to the at least one planar surface of the collagen layer, the physical coupling selected from the group consisting of a suture, a heat press adhesion, heating in the presence of a vacuum, heating in the absence of a vacuum, exposure to a heating element, exposure to heated air, or a spot weld adhesion.

7. The bioimplantable dural graft material of claim 1, wherein the at least one reinforcement layer comprises a first reinforcement layer and a second reinforcement layer, each of the first reinforcement layer and the second reinforcement layer disposed on one of the opposite planar surfaces of the collagen layer.

8. The bioimplantable dural graft material of claim 1, wherein the collagen layer comprises a first collagen layer and a second collagen layer, the at least one reinforcement layer disposed between the first collagen layer and the second collagen layer.

9. The bioimplantable dural graft material of claim 1, wherein the collagen layer comprises a thickness in the range of about 0.02 inches to 0.20 inches.

10. The bioimplantable dural graft material of claim 1, wherein the at least one reinforcement layer comprises a thickness in the range of about 0.001 inches to 0.016 inches.

11. The bioimplantable dural graft material of claim 1, wherein the at least one reinforcement layer comprises a biological agent selected from the group consisting of an antibiotic, a growth factor, a hemostasis factor, an anti-adhesion agent, or an anti-cancer agent.

12. The bioimplantable dural graft material of claim 3, wherein the bioabsorbable polymer comprises polylactic acid.

13. The bioimplantable dural graft material of claim 5, wherein the reinforcement layer physically couples to the at least one planar surface of the collagen layer, the physical coupling comprising a suture.

14. The bioimplantable dural graft material of claim 1, wherein the at least one reinforcement layer comprises a growth factor.

15. The bioimplantable dural graft material of claim 1, wherein greater than 80% of the pores have a diameter of less than 10 micrometers.

16. The bioimplantable dural graft material of claim 1, wherein greater than 95% of the pores have a diameter of less than 10 micrometers.

17. The bioimplantable dural graft material of claim 1, wherein greater than 98% of the pores have a diameter of less than 10 micrometers.

18. The bioimplantable dural graft material of claim 1, wherein substantially all of the plurality of pores have a diameter of less than 10 micrometers.

* * * * *